United States Patent
Wilkinson et al.

(10) Patent No.: US 9,389,159 B2
(45) Date of Patent: Jul. 12, 2016

(54) EXPERT-SYSTEM-BASED RHEOLOGY

(75) Inventors: John Paul Wilkinson, Gloucester (GB);
James Francis Thomas, Telford (GB);
Joanne Elizabeth Langridge,
Gloucester (GB); **Stephen John
Ritchings, Circencester (GB); Samiul
Amin**, Solihull (GB)

(73) Assignee: Malvern Instruments Ltd., Malvern,
Worcestershire (GB)

( * ) Notice: Subject to any disclaimer, the term of this patent is extended or adjusted under 35 U.S.C. 154(b) by 389 days.

(21) Appl. No.: 13/019,298

(22) Filed: Feb. 1, 2011

(65) Prior Publication Data

US 2012/0192625 A1    Aug. 2, 2012

Related U.S. Application Data

(63) Continuation of application No. PCT/GB2009/050961, filed on Jul. 31, 2009.

(51) Int. Cl.
G01N 11/14    (2006.01)
G01N 11/00    (2006.01)
G01N 35/00    (2006.01)

(52) U.S. Cl.
CPC ...... G01N 11/142 (2013.01); *G01N 2011/0006* (2013.01); *G01N 2035/00633* (2013.01)

(58) Field of Classification Search
CPC ..... G01N 11/00; G01N 11/14; G01N 11/142; G01N 11/16; G01N 2203/0094; G01N 33/30; G01N 2203/0092; G01N 11/165
USPC ........................ 73/53.05, 54.01, 54.23–54.43
See application file for complete search history.

(56) References Cited

U.S. PATENT DOCUMENTS

| | | | | |
|---|---|---|---|---|
| 3,581,558 | A | | 6/1971 | Porter |
| 4,352,287 | A | * | 10/1982 | Orth et al. ................... 73/54.39 |
| 4,484,468 | A | * | 11/1984 | Gau et al. .................... 73/54.35 |
| 5,103,679 | A | | 4/1992 | Porter |
| 5,321,974 | A | * | 6/1994 | Hemmings et al. .......... 73/54.31 |
| 6,499,336 | B1 | * | 12/2002 | Raffer ........................ 73/54.28 |
| 6,535,796 | B1 | | 3/2003 | Sierro |
| 6,725,707 | B1 | * | 4/2004 | Lin et al. ..................... 73/54.01 |
| 7,207,210 | B2 | * | 4/2007 | Moonay ...................... 73/54.28 |
| 7,275,419 | B2 | * | 10/2007 | Raffer ........................ 73/54.28 |
| 7,607,098 | B2 | * | 10/2009 | Grehlinger et al. .......... 715/762 |

(Continued)

FOREIGN PATENT DOCUMENTS

| | | |
|---|---|---|
| EP | 1219948 A2 | 7/2002 |
| JP | S4823476 | 7/1973 |

(Continued)

OTHER PUBLICATIONS

PCT Search Report WO2010/013065 A3.

(Continued)

*Primary Examiner* — David A Rogers
(74) *Attorney, Agent, or Firm* — Kristofer E. Elbing

(57) ABSTRACT

A rheometer is disclosed that includes rheometry logic that is responsive to a material selection control, to an objective selection control, to material property storage, and to process parameter storage, and is operative to assist the user with a measurement using the rheometer. In another general aspect, a rheometer includes sample history storage operative to store a history that spans a plurality of different operations performed by the rheometer on a same sample.

17 Claims, 9 Drawing Sheets

(56) References Cited

U.S. PATENT DOCUMENTS

| | | | |
|---|---|---|---|
| 8,079,250 B2* | 12/2011 | Sebok et al. | 73/54.43 |
| 2002/0138215 A1 | 9/2002 | Evans | |
| 2004/0123650 A1* | 7/2004 | Kolosov et al. | 73/54.28 |
| 2004/0173009 A1 | 9/2004 | Doe | |
| 2005/0066711 A1* | 3/2005 | Discenzo | 73/64.56 |
| 2005/0072217 A1* | 4/2005 | Discenzo | 73/53.05 |
| 2005/0145019 A1* | 7/2005 | Matsiev et al. | 73/53.01 |
| 2005/0247137 A1 | 11/2005 | Nickerson | |
| 2006/0000262 A1 | 1/2006 | Raffer | |
| 2006/0070428 A1* | 4/2006 | Bateson et al. | 73/54.32 |
| 2007/0289363 A1 | 12/2007 | Grow | |
| 2008/0173075 A1* | 7/2008 | Dale | 73/54.31 |
| 2009/0188304 A1* | 7/2009 | Eskin et al. | 73/54.35 |
| 2011/0036150 A1* | 2/2011 | Sakai | 73/54.31 |
| 2012/0096929 A1* | 4/2012 | Baek | 73/54.14 |

FOREIGN PATENT DOCUMENTS

| | | |
|---|---|---|
| JP | H06323985 | 1/1994 |
| JP | 2001066238 | 3/2001 |
| JP | 200652000 | 8/2006 |

OTHER PUBLICATIONS

"Brookfield YR-1 Rheometer," internet citation, www.brookfieldengineering.com (retrieved Jun. 3, 2004 per EPO search report).

"Yield Rheometer is Simple to Operate," internet citation, www.industrialnewsroom.com (retrieved Jun. 3, 2004 per EPO search report).

* cited by examiner rSolution
Industry overview – Personal care creams and lotions

The personal care creams and lotions industry area covers a wide range of sample types, from face creams to foot lotions. They all have similarities in that they must be manufactured from raw materials, packaged into containers, and applied to the skin or hair.
The table below outlines the processes, properties, and challenges that a typical Personal Care Cream or Lotion will see through its lifetime.

| Stage of process | Description | Challenges | Search for |
|---|---|---|---|
| Raw Materials | The raw materials used in personal care creams & lotions can include a variety of different materials. Polymers surfactants, waxes, perfumes, microencapsulated additives are a few of the ingredients commonly seen. | It is extremely important to make sure that the quality of the incoming raw materials is correct. Especially when they are sourced naturally and may have differences due to growing conditions or harvesting time. | Raw materials QC test Cole-Cole plots |
| Manufacture | This will be an emulsification process that will involve high shearing forces on the particles. It could make an oil in water emulsion (O/W) or a water in oil emulsion (O/W) or something more complex. | During this stage the correct properties must be manufactured into the product. | Manufacturing Formulation High shear rates Pumping |
| Packaging | The finished creams and lotions will be dosed into tubs or bottles or tubes ready for storage and sale. | The formulation must flow well enough to fill the container to the required volume without creating voids. The consistency of the formulation must reform while it is in the container. The filling process must be economical and quick, and ideally the product must not dribble as it is dosed into the containers. | Manufacturing Dosing into containers High speed stability |
| Storage and Transportation | Creams and lotions need good shelf life properties – they could be stored for 12 months or more and may be transported globally to reach sales destination. | Storage and transportation present two challenges. The formulation properties must not change if it is stationary for long periods, and the formulation must be robust enough to withstand low levels of agitation and changes in temperature without reduction in performance. | Storage Transportation Settling Rebuild Temperature |
| Application | To apply the product it needs to be scooped or squeezed from the container and rubbed on skin. | The overall success of a product depends on the customer's preception of it. How easy is it to remove from container? Does the product have the right consistency or thickness? How easy is it to apply to the skin? | Application Scooping Squeezing |
| Performance | The performance of the lotion or cream depends on the application of the product. Night creams are heavier than day creams, lotions can be very light. | Typical challenges in the performance are related to the feel on the skin. Does it feel sticky? Is it easy to spread? Is it easy to rub in? | Performance Rub in Skin feel |

FIG. 4

| Name | Date created | Date modified | Type | Folder |
|---|---|---|---|---|
| Personal_care_0021-Processing-predicting pumping problems.rseq | 12/06/2008 13:02:23 | 09/06/2008 10:51:27 | .rseq | Personal care (c:\ |
| Personal_care_0021-Processing-predicting pumping problems.rseq | 12/06/2008 13:11:21 | 09/06/2008 10:51:27 | .rseq | Personal Care (c:\ |
| Polymer_0007-Processing-extension.rseq | 12/06/2008 13:02:27 | 11/06/2008 14:22:02 | .rseq | Polymer (c:\Docum |
| Polymer_0007-Processing-extension.rseq | 12/06/2008 13:11:18 | 11/06/2008 14:22:02 | .rseq | Polymer (c:\Docum |

Show only: All | Sequences | Application Notes | Results | Templates

Search — processing

Advanced ▶

FIG. 5

EXPERT-SYSTEM-BASED RHEOLOGY

CROSS-REFERENCE TO RELATED APPLICATION

This application is a continuation of PCT/GB2009/050961, filed Jul. 31, 2009, which designates the United States, and it claims the benefit under 35 U.S.C. 119(e) of U.S. provisional application Ser. No. 61/137,640, filed Aug. 1, 2008, both of which are herein incorporated by reference.

FIELD OF THE INVENTION

This invention relates to rheometers and to the application of rheology.

BACKGROUND OF THE INVENTION

Rheology is the study of flow and deformation of materials. An understanding of rheology can lead to insights that are critical in order to control and optimize various industrial processes (such as pumping, extruding, etc.) and consumer processes (dispensing a shampoo, rubbing a skin cream, etc.).

Rheology by its very nature is a complex science. Accurate insights can generally only be obtained through properly set up experiments in which the sample is correctly loaded, the correct geometry is used and the actual rheometry test and test parameters are representative of the process for which the insight is required. This is inherently difficult, as in addition to an understanding of the process it requires an understanding of the material type (gel, low viscosity solution, melt, etc.) and its response to loading conditions and geometries (thixotropy, slippage, etc.).

In terms of accurately setting up the test to be representative of the process (for example pumping, spreading, etc.) an understanding is required of whether the process is shear, extension or tension, whether it is stress or strain controlled, what are the relevant shear stresses or shear rates, and so forth.

The ability to take this understanding of material and processes and accurately set up the relevant rheological test requires input from people highly skilled in experimental rheology. Conversely, the lack of properly set up and executed rheological experiments can lead to inaccurate insights being generated and an inefficient use of resources if such personnel are not available.

SUMMARY OF THE INVENTION

In one general aspect, the invention features a rheometer for measuring properties of a sample that includes a mobile part having a contact surface for contacting the sample, a fixed part having a contact surface for contacting the sample, a vertical actuator for providing relative vertical motion between the mobile part and the fixed part, and a rotary actuator for providing relative rotary motion between the mobile part and the fixed part. The rheometer also includes material property storage that stores at least one property for each of a plurality of materials, process parameter storage that stores at least one parameter for each of a plurality of processes, a material selection control operative to receive a material selection for use as the sample, and an objective selection control operative to receive an experimental objective selection. Rheometry logic is responsive to the material selection control, to the objective selection control, to the material property storage, and to the process parameter storage, and is operative to assist the user with a measurement using the rheometer.

In preferred embodiments, the material selection control and the objective selection control can be part of a user interface for the rheometer. The rheometry logic can include a geometry selection output operative to provide the user assistance by communicating a selected geometry selection for the mobile part. The rheometry logic can include parameter generation logic operative to provide the user assistance by providing test parameters for the rheometer. The rheometry logic can include option generation logic operative to provide the user assistance by providing a list of testing options for a particular set of parameters for the rheometer. The rheometry logic can include control logic operative to provide the user assistance by controlling parts of the rheometer. The rheometry logic can include sequence generation logic operative to generate a control sequence for the rheometer. The control sequence can be generated by retrieving a stored sequence from the process parameter storage. The rheometer can further include a sequence editing interface for editing generated control sequences. The control logic can be operative to control the rotary actuator and the vertical actuator. The control logic can be operative to control the temperature for a test. The rheometry logic can be further responsive to user-entered parameters. The rheometry logic can be further responsive to test results from the rheometer. The rheometry logic can be further responsive to an identification signal that identifies an attribute of the rheometer. The identification signal can identify an environmental control module. The process storage can be organized by industry.

In another general aspect, the invention features a rheometer for measuring properties of a sample that includes a mobile part having a contact surface for contacting the sample, and a fixed part having a contact surface for contacting the sample. The rheometer also includes a vertical actuator for providing relative vertical motion between the mobile part and the fixed part, and a rotary actuator for providing relative rotary motion between the mobile part and the fixed part. Sample history storage is operative to store a history that spans a plurality of different operations performed by the rheometer on a same sample.

In preferred embodiments the rheometer further includes rheometry logic responsive to the sample history storage and operative to derive selections of further operations to perform on the sample based on the stored sample history. The rheometry logic can further include control logic operative to control the rheometer based on the derived selections. The control logic can be operative to continuously control the rheometer based on a continuously updated sample history.

Systems according to the invention can be advantageous in that they can assist users in setting up rheology experiments. This can speed up the selection of experiments, provide increased accuracy in the results of experiments, and may even allow relatively inexperienced users to achieve meaningful results. Providing for sample history to be stored in an rheometer can also help users make more precise and insightful measurements.

BRIEF DESCRIPTION OF THE DRAWINGS

FIG. 4 is a screenshot of a search listing of application notes for a particular skin cream problem for the rheometer of FIG. 1;

FIG. 5 is a screenshot of a search listing of sequences for the skin cream problem presented in connection with FIG. 4 for the rheometer of FIG. 1;

DETAILED DESCRIPTION OF AN ILLUSTRATIVE EMBODIMENT

Figure 1:
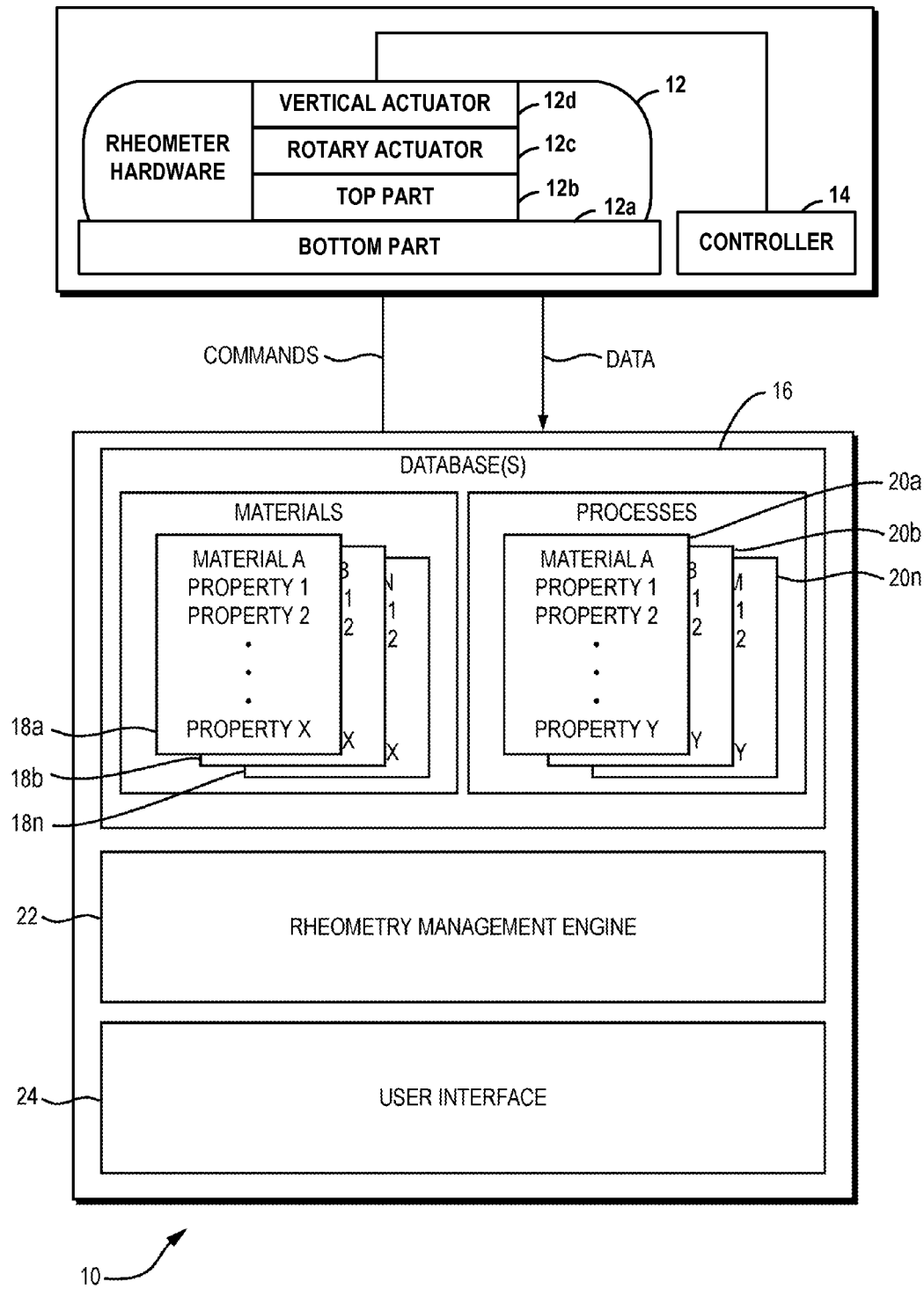
FIG. 1 is a block diagram of a rheometer according to the invention.

Referring to FIG. 1, an illustrative rheometer 10 includes rotary rheometer hardware 12 and a controller 14 that performs low-level control and oversight functions. As is well known, the rheometer hardware typically includes a top part 12a and a bottom part 12b with a vertical actuator 12d for providing relative vertical motion between the mobile part and the fixed part, and a rotary actuator 12c for providing relative rotary motion between the mobile part and the fixed part.

The rheometer also includes storage 16, such as a database, for material and process information. The materials database includes a number of entries 18a, 18b, ... 18n for a number of different materials, and each entry includes information about that material, such as its properties. The process database includes a number of entries 20a, 20b, ... 20n about a number of different processes, and each entry includes information about that process, such as parameters that are important in setting up rheological tests.

The rheometer also includes a rheometry management engine 22. The rheometry management engine interacts with the database(s), a user interface 24 for the rheometer, and the rheometer hardware. In this embodiment, the rheometer hardware and controller are housed in a chassis, and the databases, rheometry management engine, and user interface are implemented with a standalone computer workstation running a standard operating system and special-purpose software. It is also possible to create an implementation that is based on specialized custom hardware, or a combination of the two approaches.

The various elements and steps described can be reorganized, divided, and combined in different ways without departing from the scope and spirit of the invention. For example, all parts of the system could be integrated into a single chassis, or program logic could be split into different functional sub-parts. The database can range from a collection of files to a more powerful and feature-rich database.

In operation, the rheometry logic can provide a rheometry-specific assistance to the user through the material and process information stored in the database(s) based on user-supplied experimental objectives. It can achieve this goal through the use of various types of well-known methodologies, such as inference engine technology. The exact approach employed will depend on a variety of implementation issues, such as the types of applications supported.

Types of assistance provided and can include selecting a geometry for a particular material based on its stored properties, suggesting test parameters for a particular type of experiment, selecting data sets relevant to a particular objective, or even directly controlling the rheometer. It is also possible for the rheometer to create a control sequence for the rheometer, which can be used directly or edited. The rheometry logic can also use an identification signal provided by interchangeable parts of the rheometer, such as environmental control modules, in a providing its assistance to the user. Interchangeable cartridges are discussed in more detail in a commonly owned applications entitled RHEOMETER WITH MODULAR ENVIRONMENTAL CONTROL SYSTEM, Ser. Nos. 61/137,639, 12/462,337, and PCT/GB2009/050959, now U.S. Pat. No. 8,225,644.

As discussed above, prior art systems tend to require its users to be people highly skilled in experimental rheology and to have an understanding of material and processes to accurately set up a relevant rheological test. But these are skills that are not commonly encountered in a wide range of industries. Rheometers equipped with the type of rheometry logic described in connection with this embodiment can help even relatively unskilled users to achieve better experimental results.

One example of the need for assistance is for a rheological phenomena known as thixotropy. A large proportion of materials that are measured using a rheometer are thixotropic—their internal structure breaks down as they are sheared and require a finite time to rebuild the original structure. The act of placing the sample onto the rheometer can disturb its structure and reduce the accuracy and repeatability of the rheological testing. Loading the sample can, in extreme cases, be the largest influence on data accuracy.

The sample is loaded onto the rheometer and the measurement head of the rheometer is lowered into the sample. This process can exert stresses and strains onto the sample that are quite large and that can easily disturb the sample's structure. All of this happens before a test is even started. The results of the test can be greatly affected by the strain history—what has happened to the sample before the point at which it is being tested.

Figure 2:
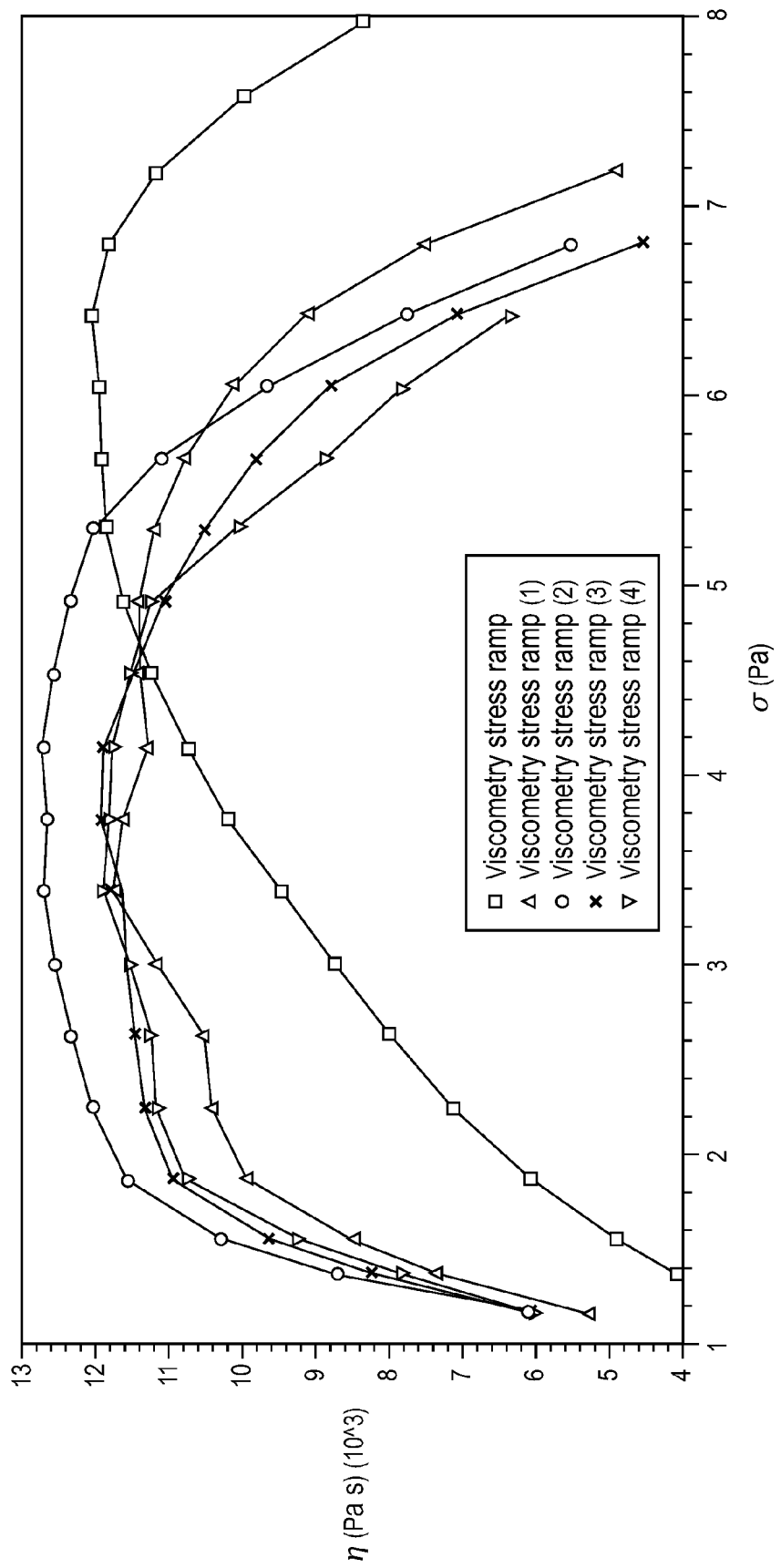
FIG. 2 is a family of plots of viscosity against shear stress for a skin cream sample.

Referring to FIG. 2, the importance of sample history is illustrated by a series of experiments in which a skin cream is exposed to a stress ramp. The only difference between these plots results from a different level of initial stress on the sample. This is due to the fact that many material systems tested on a rheometer structures that are very sensitive to stresses and/or strains that they experience, and these changes in the structure impact measured rheological responses. Having well-defined and prescribed loading protocols (based on information in the material database) and having knowledge of the sample throughout the experiment becomes extremely useful—both to get consistent results as well as to get insights on the sensitivity of the material structure to various stresses and/or strains and the corresponding rheological response. In this example, knowledge of the process (pumping) and the knowledge of the material database (skin creams) come together to give a solution to a user's problem in a rheologically sound and robust manner.

Figure 3:
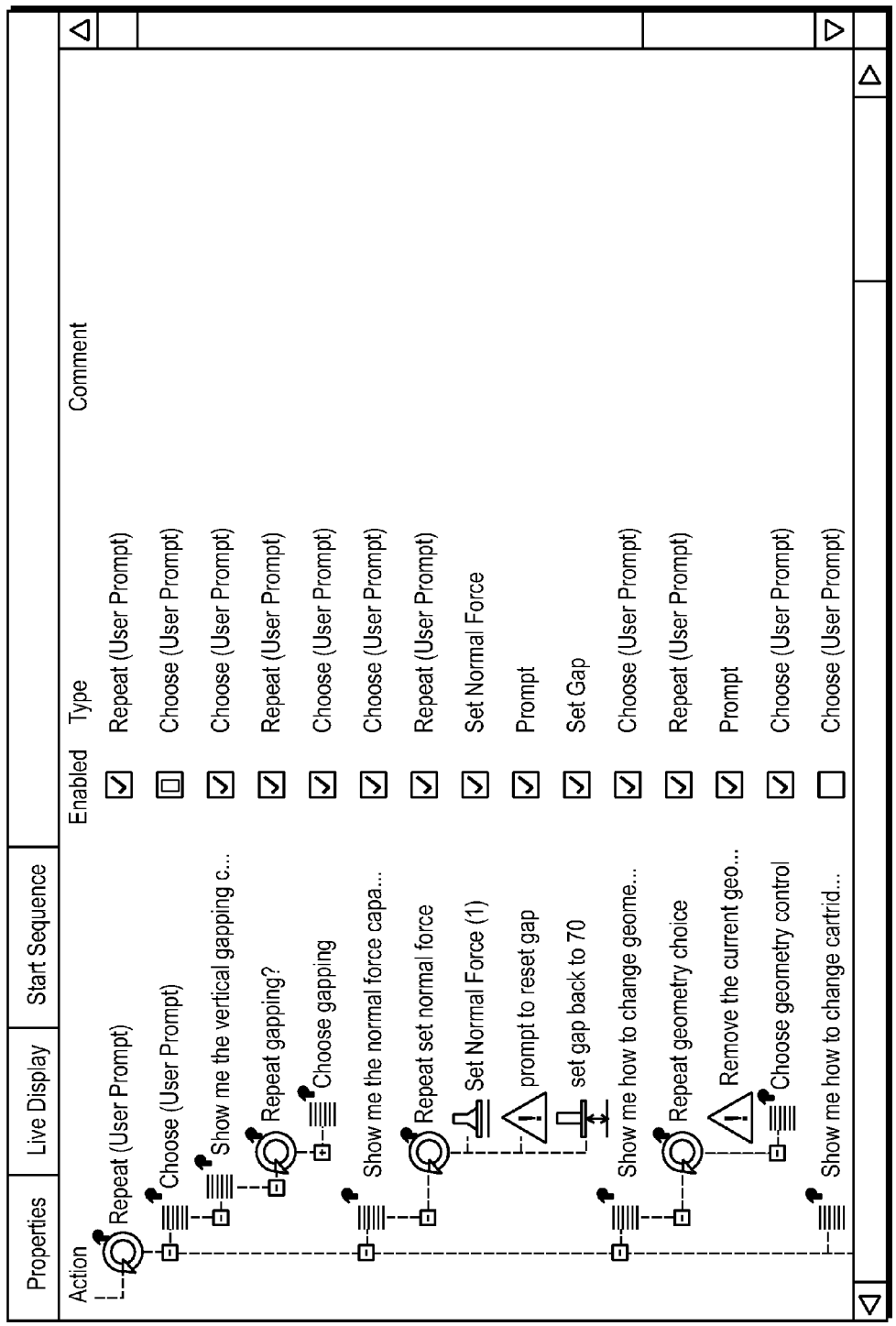
FIG. 3 is a screenshot of a sequence authoring screen for the rheometer of FIG. 1, showing a simple demo sequence.

Referring to FIG. 3, the use of the illustrative rheometer to investigate these skin care problem now be discussed in more detail. The rheometer bases its tests on fully programmable sequences. These sequences can be made up of a variety of constructs, including instrument actions, prompts, and displays, as well as other conventional programming constructs. Sequences can be developed by any appropriate party, such as the rheometer manufacturer, a consultant, or an end-user.

Figure 6:
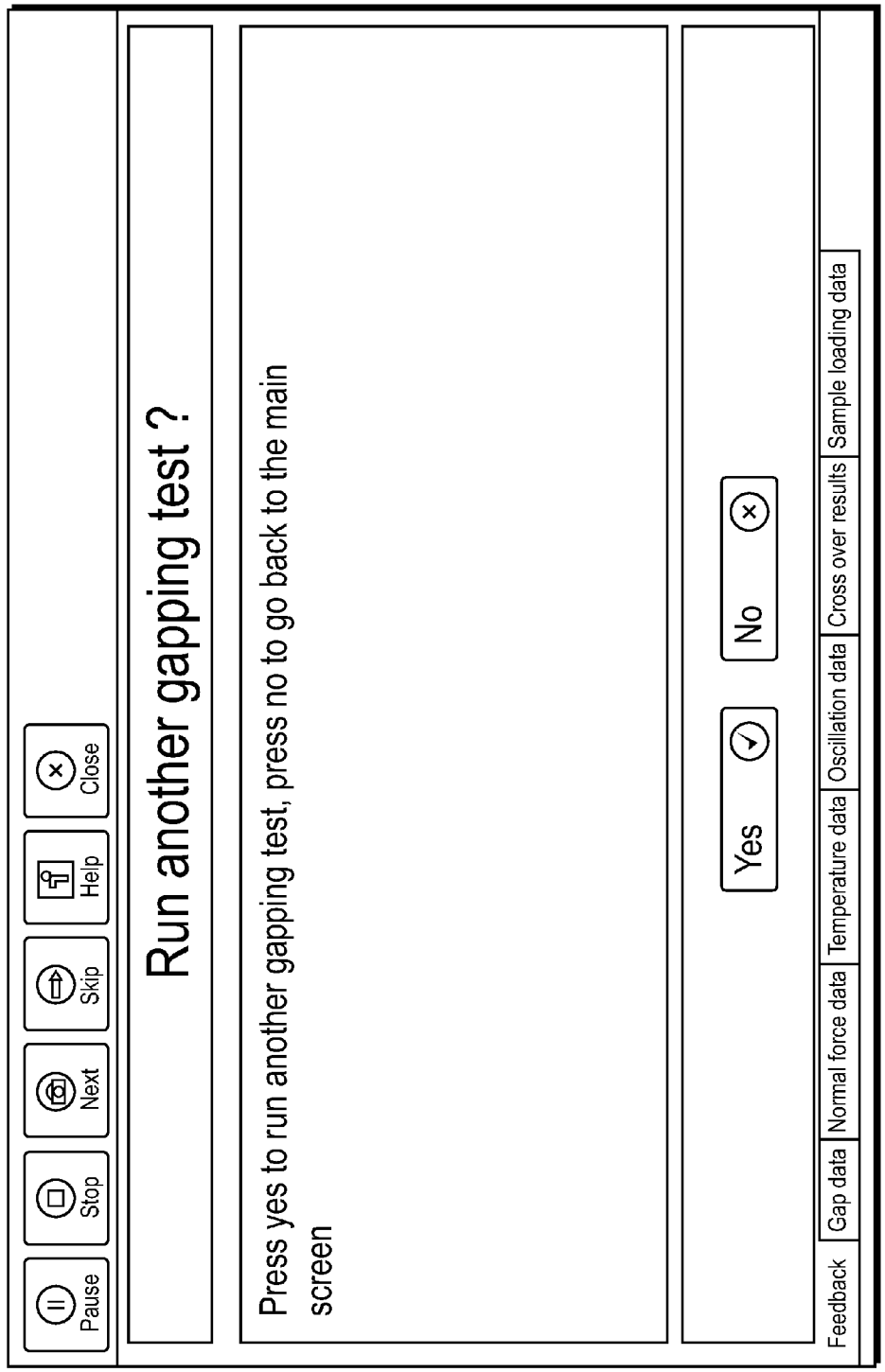
FIG. 6 is a screenshot of an illustrative prompting screen for the rheometer of FIG. 1.

Referring to FIG. 4, the user can search the rheometer's database for "personal-care overview," for example, and the system will return a list of pertinent application notes. Referring to FIG. 5, after reviewing these notes, the user can narrow his or her search to find individual sequences. The user can then select an appropriate sequence and run it. This sequence will explain and walk the user through an experiment appropriate to his or her objective. Referring to FIG. 6, the rheometer may present prompt screens during the sequence to prompt the user to perform certain operations, such as setting the system geometry or changing an environmental control cartridge. The sequence can also perform many operations without the user's help, such as setting a temperature, or running a test.

Figure 7A:
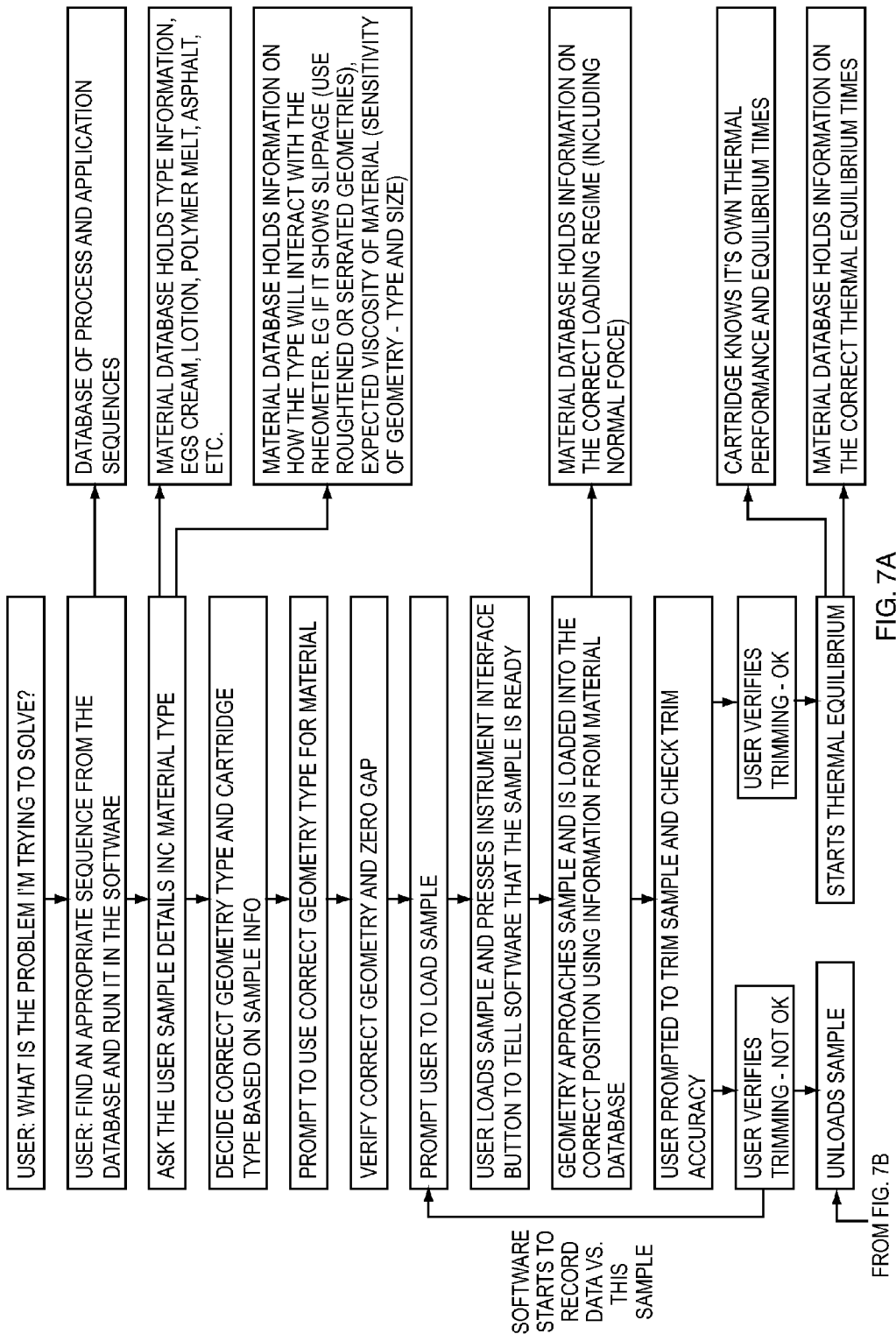
FIGS. 7A-7C are a flowchart illustrating the operation of the rheometer of FIG. 2.
Figure 7B:
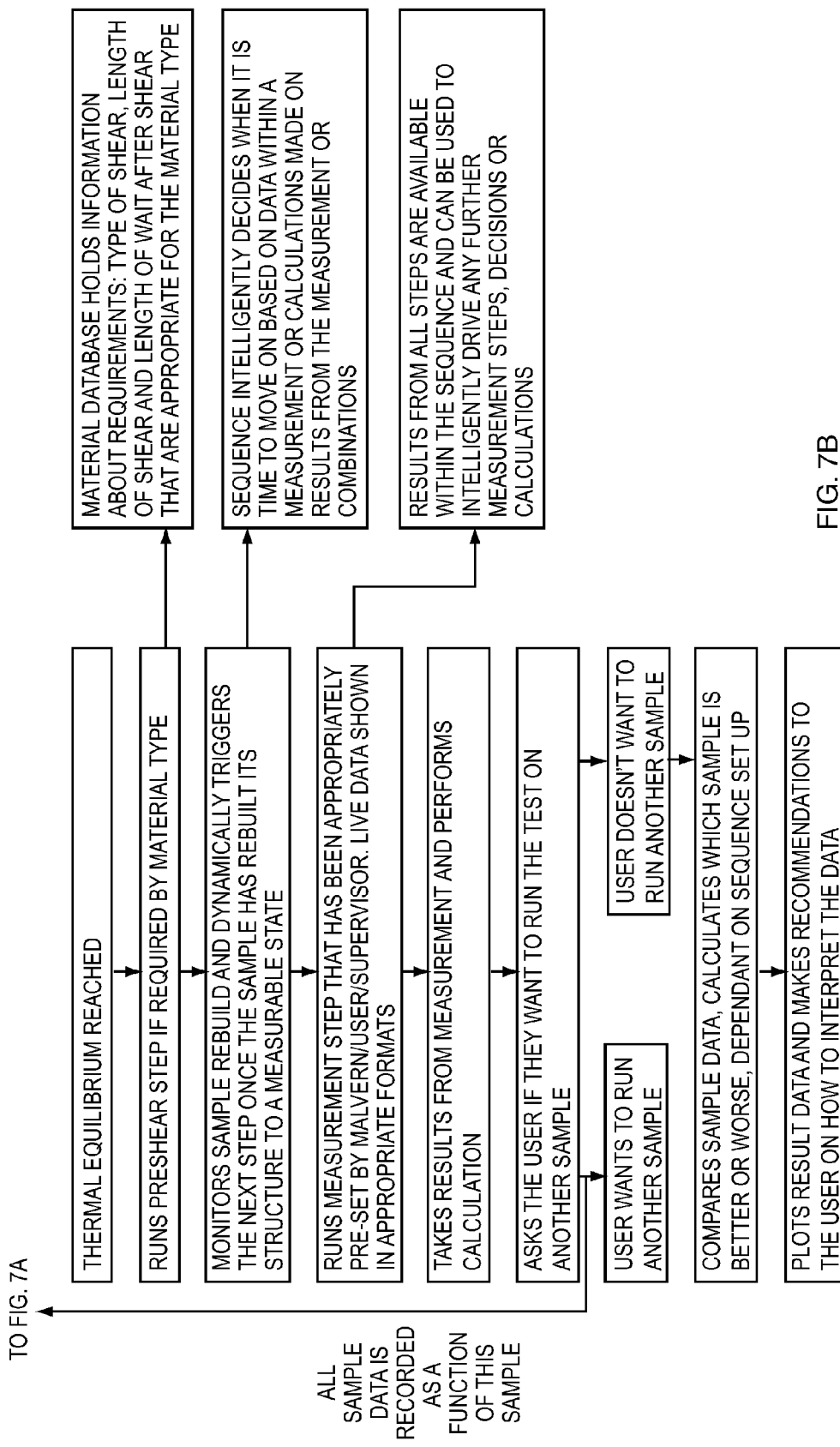
Figure 7C:
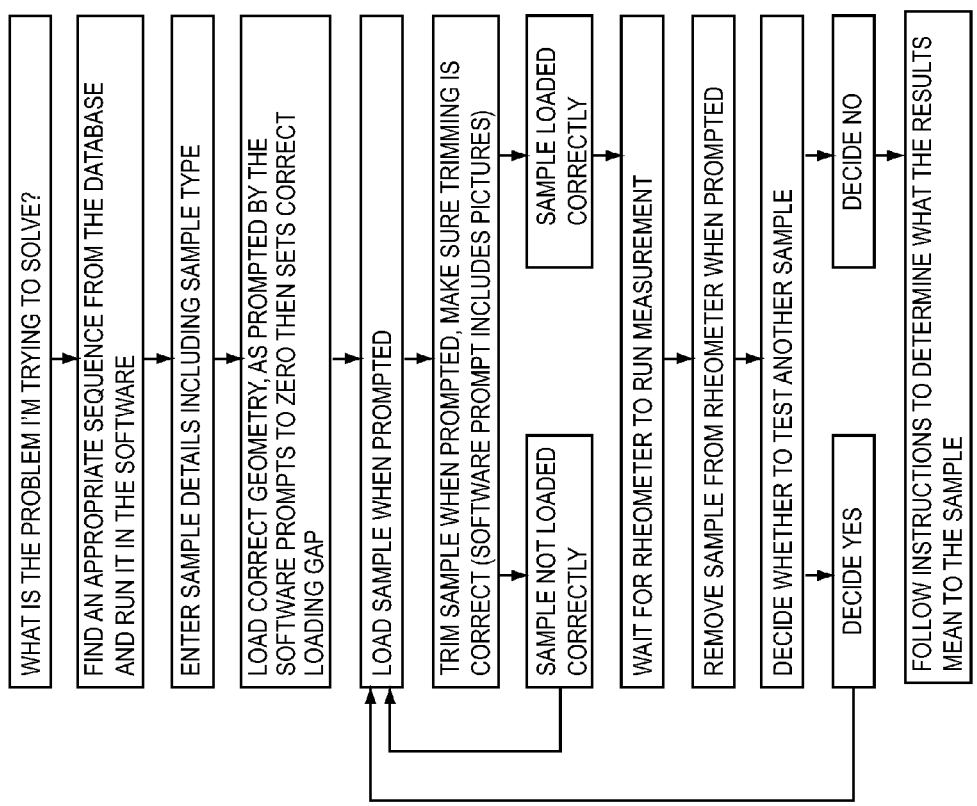

A flowchart illustrating a detailed sets of operations illustrating the solution of an industry-specific problem is also outlined in FIGS. 7A-B and 7C. Actions in the left column are performed by the rheometer unless otherwise specified, although some steps could be provided by either the user or the rheometer. For example, the rheometer can set a temperature or it can prompt the user to set a temperature. Blocks in the right column indicate how expert rheometry knowledge can be applied to individual steps.

Systems according to the invention can provide a comprehensive material and process database, with all rheologically relevant parameters having been generated and linked with instrumental, geometry and loading parameters for accurate sample loading, geometry selection and automatic test configuration, set up, and execution.

The material database can be a comprehensive database of materials which are industrially relevant and which are appropriate for rheological characterization. These can include polymers, various complex fluids (colloidal suspensions, emulsions, foams, self-assembling systems, biofluids) asphalt, fuel, oils, pharmaceutical and personal care creames and lotions, food products, such as mayonnaise, ketchup, yogurt, etc.

The information contained in the material database may include properties such as:
  Expected range of viscosity
  Size of Particles Present
  Thixotropy in the Sample
  Slippage in the sample
  Sample Loading Temperature
  Sample Loading Normal Force
  Test temperatures and equilibrium values
  Density
  Physical transition points
  Shelf life
  Preshear parameters The process database can be a comprehensive database of rheology-relavant processes across a range of different industries, each sequence can be application specific and pre-programmed with appropriate rheological tests for the problem, appropriate settings for important parameters, and appropriate geometry information so that a novice user can make reliable and correct rheological measurements on their sample. Illustrative categories of processes can include:
  Home and Personal Care
  Foods
  Paints and Coatings
  Pharmaceutical and Drug Delivery
  Medical
  Nanotechnology
  Petrochemical
  Speciality Chemicals
  Cement and Ceramic In addition, some processes that are especially relevant for a range of material types, such as polymers (melts and solutions), complex fluids (colloidal suspensions, emulsions, foams, self-assembling systems, biofluids) asphalt, are included. Process and Material information can be populated in a number of ways, such as by the instrument manufacturer, by the user, or based on industry or company standards.

The following are some specific software/hardware features that can allow the accurate sample loading, geometry selection and automatic test configuration, set-up and execution (Intelligent Rheometry Linking Mechanism):

Fully programmable software interface—The software can configure the rheological test as a sequence of actions that can be put together in an order appropriate for the requirements of the customer's sample. Instrument and material parameters are exposed to the sequence and can be used within the sequence for intelligent decision making. Parameters are available from various sources, including but not limited to the material database, the instrument parameters and settings, measurement geometry settings, results from within the sequence, and user entered variables which can be combined at design time to create a self-modifying test that automatically uses the correct settings.

Absolute knowledge of sample history—The software can be configured in such a way that all temperature, gap, normal force and stresses and strains that have been exerted on the sample since it was placed in the rheometer are measured and recorded. These can be plotted against the time scale of the experiment (useful for comparing thixotropic samples) or against the time scale of some internal or external parameter (e.g. when the sample was manufactured or mixed or put onto the rheometer—regardless of how many experiments have been made on it.

Dynamic control of the gap and normal force parameters by the digital system-Intelligent control loop for the Normal Force (NF) and gap settings. Normal force and gap are important parameters for complete sample knowledge. Rheology is a 3D science, and much can be gained from a complete knowledge of the actual geometry of the sample while it is being measured, as well as the vertical force that has been/is being exerted on it or by it. The instrument uses a digital control loop which accurately controls the normal force and the gap throughout the sample's time on the rheometer. These parameters can be set dynamically through the sequence according to the type of sample and geometry being used. Digital control of rheometers is described in a commonly-owned application entitled RHEOMETER CONTROL SYSTEM, Ser. Nos. 61/137,670 and PCT/GB2009/050962, and US Publication No. 20120240655.

EXAMPLES

A few examples of how the rheometer can be used follow.
Loading, Geometry:
  Dynamic recommendation of geometry to use based on parameters such as whether the sample is thixotropic, how big the particles in it are and the expected range of viscosity.
  Automatic setting of the gapping profile used or the maximum normal force used for a certain sample and geometry combination.
Process Relavant Test
  Industry-Personal Care, Process-Pumpability of Skin Creames-link to process database—automatic loading of Yield Stress Test—will guide user through choice of appropriate geometry and accurate loading of sample (link to material database), and then run stress ramp to determine yield stress. Documentation on link of yield stress to pumpability will automatically load.
Rheological Best Practice Used within the Test
  Each part of the sequence can be set with parameters that will stop the test if certain rheological criteria have been reached—e.g. an automatic recognition of the end of the linear viscoelastic region (LVER) can be used to make sure the sample isn't over strained so that further tests can be made on the same sample, a value from within the LVER can then be used in all subsequent testing in the sequence to make sure that the data being measured is within the LVER (or outside it, if desired).

Generally, the embodiments described can provide a method whereby accurate sample loading and geometry selection is accomplished through software/hardware features that allow appropriate parameters to be adjusted based on the sample, including, but not restricted to the geometry selection parameters, gapping profile, maximum normal force. These are determined through linking with a comprehensive material database.

The embodiments described can also provide a method whereby accurate rheological test configuration, set up and execution is automatically accomplished through a fully programmable software interface that allows test type and test parameters to be determined and loaded in through linking with a comprehensive process database. They may also provide a method whereby the sequence of testing can be dynamically altered to suit the sample based on the sample database parameters and their interaction with other parts of the system, software and sequence as it runs. As used in a comprehensive, sample type specific, process database.

The present invention has now been described in connection with a number of specific embodiments thereof. However, numerous modifications which are contemplated as falling within the scope of the present invention should now be apparent to those skilled in the art. It is therefore intended that the scope of the present invention be limited only by the scope of the claims appended hereto. In addition, the order of presentation of the claims should not be construed to limit the scope of any particular term in the claims.

What is claimed is:

1. A rheometer for measuring properties of a sample, comprising:
    a mobile part having a contact surface for contacting the sample, a fixed part having a contact surface for contacting the sample, a vertical actuator for providing relative vertical motion between the mobile part and the fixed part,
    a rotary actuator for providing relative rotary motion between the mobile part and the fixed part,
    a controller operative to dynamically control the mobile part by driving the vertical actuator and the rotary actuator during each of a plurality of predetermined rheometric operations for the mobile part from a control sequence,
    sample history storage operative to store a history of a plurality of different rheometric operations performed on a same sample by the rheometer that include at least one rheometric operation performed by the mobile part of the rheometer under control of the controller, and
    rheometry logic responsive to the sample history storage and operative to derive a sequence of further different rheometric operations to be performed by the mobile part of the rheometer on the sample under control of the control logic to test the sample based on the stored sample history.

2. The apparatus of claim 1 wherein the rheometry logic is operative to derive selections of further operations based on past strain on the sample.

3. The apparatus of claim 1 wherein the rheometry logic is operative to derive selections of further operations based on past strain on the sample so as to ensure that the further operations don't overstrain the sample.

4. The apparatus of claim 1 wherein the rheometry logic is operative to derive selections of further operations based on past strain on the sample so as to ensure that the further operations keep the sample within its linear viscoelastic region.

5. The apparatus of claim 1 further including control sequence storage operative to store control sequences and wherein the controller is responsive to the control sequence storage.

6. The apparatus of claim 1 further including a user interface responsive to user input to edit control sequences stored in the control sequence storage.

7. The apparatus of claim 1 wherein the history storage is operative to store a history of rheometric operations that includes temperature, gap, normal force and stresses and strains that have been exerted on the sample since it was placed in the rheometer.

8. The apparatus of claim 7 wherein the history storage is operative to store a history or rheometric operations that includes all temperature, gap, normal force and stresses and strains that have been exerted on the sample since it was placed in the rheometer.

9. The apparatus of claim 1 wherein the controller is operative to apply a control law based on a received target signal.

10. The apparatus of claim 9 wherein the controller is operative to apply a proportional control law based on a received target gap signal.

11. The apparatus of claim 1 wherein the control logic is further operative to control the temperature for a test.

12. A rheometry method for measuring properties of a sample, comprising:
    providing a mobile part having a contact surface for contacting the sample,
    providing a fixed part having a contact surface for contacting the sample,
    providing a vertical actuator for providing relative vertical motion between the mobile part and the fixed part,
    providing a rotary actuator for providing relative rotary motion between the mobile part and the fixed part,
    providing sample history storage,
    performing a first predetermined rheometric operation on the sample with the mobile part of the rheometer,
    dynamically controlling the mobile part during the step of performing the first predetermined rheometric operation on the sample with the mobile part of the rheometer,
    performing a second predetermined rheometric operation on the sample,
    recording in the sample history storage a history of rheometric operations that spans the first and second rheometric operations performed on the same sample, and
    deriving a sequence of further operations to be performed by the mobile part of the rheometer on the sample based on the stored sample history.

13. The method of claim 12 further including controlling the rheometer based on the derived selections.

14. The method of claim 12 further including contiuously controlling the rheometer based on the derived selections.

15. The method of claim 12 wherein the step of deriving derives selections of further operations based on past strain on the sample caused by the first and second rheometric operations.

16. The method of claim 12 wherein the step of deriving derives selections of further operations based on past strain on the sample caused by the first and second rheometric operations so as to ensure that the further operations don't overstrain the sample.

17. The method of claim 12 wherein the step of deriving derives selections of further operations based on past strain on the sample caused by the first and second rheometric operations so as to ensure that the further operations keep the sample within its linear viscoelastic region.

\* \* \* \* \*